(12) United States Patent  (10) Patent No.: US 7,572,267 B2
Manzo  (45) Date of Patent: Aug. 11, 2009

(54) METHOD AND APPARATUS FOR RADICAL PROSTATECTOMY ANASTOMOSIS INCLUDING AN ANCHOR FOR ENGAGING A BODY VESSEL AND DEPLOYABLE SUTURES

(75) Inventor: Scott E. Manzo, Shelton, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 843 days.

(21) Appl. No.: 10/550,700

(22) PCT Filed: Apr. 16, 2003

(86) PCT No.: PCT/US03/11915

§ 371 (c)(1),
(2), (4) Date: Sep. 27, 2005

(87) PCT Pub. No.: WO2004/098418

PCT Pub. Date: Nov. 18, 2004

(65) Prior Publication Data

US 2007/0010832 A1 Jan. 11, 2007

(51) Int. Cl.
*A61B 17/12* (2006.01)
(52) U.S. Cl. ........................ 606/144; 606/153
(58) Field of Classification Search ................ 606/144, 606/148, 151, 153–156, 232; 623/2.4, 2.41, 623/13.13, 13.14, 19.11, 23.72
See application file for complete search history.

(56) References Cited

U.S. PATENT DOCUMENTS 5,545,171 A 8/1996 Sharkey et al.
6,017,352 A * 1/2000 Nash et al. .................. 606/153
6,190,396 B1 * 2/2001 Whitin et al. ............... 606/144
6,346,111 B1 * 2/2002 Gordon et al. .............. 606/144

OTHER PUBLICATIONS

International Search Report for PCT/US03/11915, date of Mailing Dec. 18, 2003 (3 pgs).

* cited by examiner

*Primary Examiner*—Todd E Manahan
*Assistant Examiner*—Jennifer L Hornberger

(57) ABSTRACT

A radical prostatectomy anastomosis device including a cartridge having a plurality of anchors (174) slidably disposed in a plurality of distally angled radial channels formed in the cartridge and a pusher assembly operatively coupled within the cartridge. The pusher assembly being configured and adapted to push each of the plurality of anchors out of the angled radial channels of the radial cartridge. The device further including a fitting (104) removably coupled to a distal end of the cartridge. The fitting including a flange (162) having a plurality of holes (164) formed radially around the flange, wherein each of the plurality of holes includes suture locking means (166) configured and adapted to permit a suture to be drawn distally through each of the plurality of holes and to prevent the sutures from being drawn proximally through each of the plurality of holes. The device further including a plurality of sutures (182) secured to an inner surface of the cartridge. The sutures passing through the fitting, through a respective hole of the plurality of holes formed in the fitting and secured to an outer surface of a respective anchor.

28 Claims, 19 Drawing Sheets

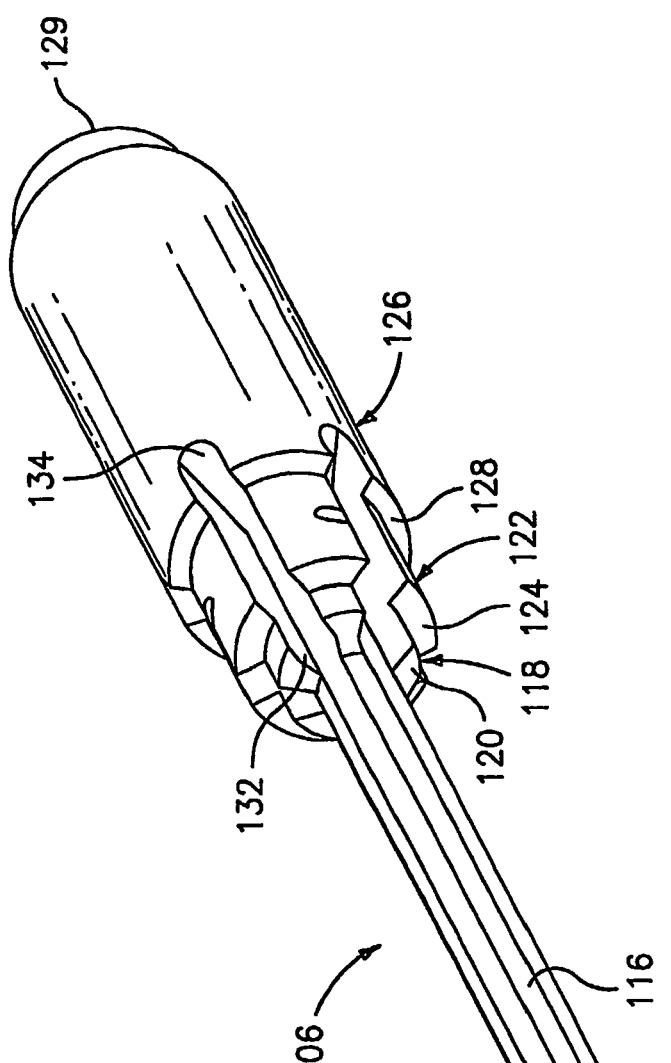
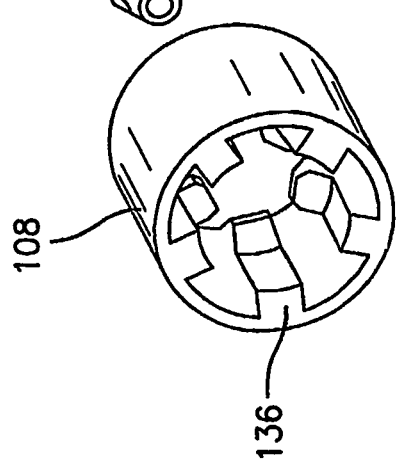
FIG. 11
FIG. 10

METHOD AND APPARATUS FOR RADICAL PROSTATECTOMY ANASTOMOSIS INCLUDING AN ANCHOR FOR ENGAGING A BODY VESSEL AND DEPLOYABLE SUTURES

BACKGROUND

1. Technical Field

The present disclosure relates to a device for anastomosing two hollow body parts and, more particularly to methods and apparatus for anastomosing a patient's urethral stump to a patient's bladder following the removal of the patient's prostate during a radical prostatectomy.

2. Background of Related Art

Most body conduits are generally cylindrical in configuration and have a circular cross-section. When it is desirable to suture such a conduit, typically for attachment to another body conduit, the sutures are placed around the circumference of the conduit in order to maintain the patency of its lumen or channel. This type of attachment is commonly referred to as an anastomosis. It can be appreciated that the sutures made on top of the conduit in an anastomosis are made relatively easier than the sutures made underneath the conduit.

The complexity of anastomosis attachment is made manifestly apparent in a surgical procedure referred to generally as a radical prostatectomy (i.e., a well established surgical procedure for patients with localized prostatic carcinoma). There are primarily two types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, next to the external urethral sphincter. The prostatic urethra is divided at this point; then the prostatic urethra and the prostate gland through which it goes are pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and approximated against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult. This difficulty is complicated by the tendency of the urethral stump to retract into adjacent tissue. As a result, considerable time and effort must be expended to re-expose the urethral stump and begin the anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179 issued to Edelstein there is disclosed a suturing device including a shaft with portions defining an interior channel extending between the proximal and distal ends of the shaft. This channel includes a generally axial lumen which extends to the proximal end and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164 issued to Roth there is disclosed a suture guide with a curved distal portion. This distal portion has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039 issued to Avant et al. there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stub to the bladder neck easier. As such, each surgical procedure using the prior art devices is still time consuming and continues to require great skill in order to be performed. Moreover, none of these prior art devices will potentially lead to a water tight anastomosis. Nor do these prior art references disclose a suture device which can accurately position a plurality of anchor and suture combinations, for use at or near the severed end of a body conduit, simultaneously. Accordingly, the need exists for a radical prostatectomy anastomosis device which overcomes the drawbacks of the prior art devices and which is quick and simple to use thereby enabling those with lesser skill to perform the procedure. In particular, the need exists for a radical prostatectomy anastomosis device which uses bio-absorbable implantable anchors to secure the bladder to the urethra following a radical prostatectomy and which anchors are gradually absorbed into the body.

SUMMARY

The presently disclosed method and apparatus addresses these difficulties of the prior art. A device for joining a first body vessel with a second body vessel comprises an anchor fitting having a flange for engaging the first body vessel. The flange includes a plurality of holes formed therethrough. The device includes a cartridge having an aperture and removably coupled to a proximal end of the anchor fitting. The cartridge includes: a body having a distal end and a plurality of longitudinal channels defined in the body, each longitudinal channel being open on the body at the distal end; a plurality of drive wires adapted to be received in a respective one of the longitudinal channels of the body; a plurality of needle anchors adapted to be seated within a respective one of the channels, each of the needle anchors having a pointed distal end. The device includes a plurality of sutures. Each suture is secured to one of said needle anchors, threaded through one of the holes formed in the flange of the anchor fitting and through the aperture of the cartridge.

Certain embodiments include a suture lock provided in each of the holes. The suture lock is adapted to permit the sutures to be drawn distally through the holes and to prevent the sutures from being withdrawn proximally through the holes.

The flange may include a plurality of anchoring members formed along a proximal surface thereof for engaging a body vessel. A hub may be disposed on the body and arranged for engaging the drive wires, the drive wires being displaced distally by distal movement of the drive wires. The anchor fitting is preferably made of a bioabsorbable material and each of the plurality of needle anchors is preferably made of a bioabsorbable material. Each of the plurality of sutures is preferably made of a bioabsorbable material.

In a further aspect of the present invention, an anastomosis device comprises a cartridge having an aperture and having a plurality of needle anchors slidably disposed in a plurality of channels formed in the cartridge and a pusher assembly adapted to push each of the plurality of needle anchors out of the channels of the cartridge. An anchor fitting is removably coupled to a distal end of the cartridge, the anchor fitting including a flange having a plurality of holes. Each of the plurality of holes includes a suture lock adapted to permit a suture to be drawn distally through each of the plurality of holes and to prevent the sutures from being drawn proximally through each of the plurality of holes. The device has a plurality of sutures passing through a respective hole of the plurality of holes and secured to a respective needle anchor, and extending through the aperture of the cartridge.

The cartridge desirably further comprises a body having an enlarged distal end and a plurality of longitudinal channels, wherein each longitudinal channel terminates in an angled channel. The pusher assembly may comprise: a hub adapted to be received on the body, the hub including a flange formed at a proximal end thereof; and a plurality of drive wires received in a respective one of the longitudinal channels. Each drive wire terminates in an angled distal tip corresponding to the angled channels. The drive wires are disposed adjacent the hub so that distal movement of the hub moves the drive wires distally.

The pusher assembly may further comprise a compression spring disposed around the central shaft and between the flange of the hub and a distal end of the body. Each of the needle anchors may be adapted to be seated on a respective angled distal tip of the plurality of drive wires so that distal movement of the hub along the central shaft drives the plurality of angled distal tips against the needle anchors seated thereon and expels the needle anchors from the channels.

The cartridge may include a cover for enclosing the body and the pusher assembly therein. The cover may include a proximal head arranged for engagement by an instrument. The anchor fitting, needle anchors and sutures are preferably made of a bio-absorbable material.

The flange of the anchor fitting desirably includes a plurality of anchoring members formed on a proximal surface thereof.

In a further aspect of the present invention an anastomosis device comprises a cartridge having a plurality of needle anchors retained therein and a pusher assembly slidably disposed within the cartridge. The pusher assembly is arranged to engage each needle anchor and to deploy the plurality of needle anchors out of the cartridge by moving the pusher assembly distally within the cartridge. The device has an anchor fitting for engaging a body vessel including an annular sleeve operatively coupled to a distal end of the cartridge and a flange formed on a distal end of the annular sleeve. The flange includes a plurality of holes formed therein with each hole having a suture lock. The device has a plurality of sutures, wherein a single suture is secured to a respective needle anchor and extends through a respective hole in the flange of the anchor fitting, and proximally through the annular sleeve of the anchor fitting, so that when the cartridge is separated from the anchor fitting, the sutures are drawn proximally through the anchor fitting thereby drawing the needle anchors toward the anchor fitting.

The anchor fitting may further comprise a body and an enlarged distal end, and a plurality of longitudinal channels for receiving the needle anchors. The longitudinal channels desirably include distally angled channels formed in the enlarged distal end for receiving the needle anchors therein. The pusher assembly may further comprise a hub slidably received on the body and a plurality of drive wires wherein each of the drive wires is configured and adapted to be received in a respective one of the longitudinal channels of the body.

The anchor fitting may further comprise a compression spring disposed about the central shaft and the drive wires and between the hub of the pusher assembly and a proximal surface of the body. The cartridge may further comprise a cover configured and adapted to enclose the central shaft and the pusher assembly therein and the cover may include a proximal head.

The flange of the anchor fitting desirably includes a plurality of anchoring members formed on a proximal surface thereof.

The suture lock is desirably configured and adapted to permit the sutures to be drawn distally through the holes formed in the flange and to prevent the sutures from being withdrawn proximally through the holes.

In a further aspect of the present invention, a method of approximating a first body vessel with a second body vessel comprises: inserting an anchor fitting of an anastomosis device into the first body vessel; passing an instrument into the second body vessel; coupling the instrument to the anastomosis device; disposing the anastomosis device within the second body vessel so that needle anchors of the anastomosis device are within the second body vessel; deploying the needle anchors from the anastomosis device into the second body vessel; and withdrawing the sutures proximally, the sutures being attached to the needle anchors, and threaded through the anchor fitting, so that the needle anchors and the anchor fitting are moved toward one another.

The method desirably includes withdrawing the instrument thereby separating the anchor fitting from the device and tightening the anastomosis by drawing the sutures through an annular sleeve of the anchor fitting.

In yet another aspect of the present invention, an anastomosis device comprises: an anchor fitting having a collar and a flange extending radially outward therefrom, the flange includes a plurality of opening formed therein, wherein each opening includes a suture lock configured and adapted to permit unidirectional passage of a suture therethrough; a cartridge removably coupled to a proximal end of the fitting, the cartridge including: a body having a plurality of substantially longitudinally oriented channels with a distal end of each channel terminating in a radially angled channel; a pusher having a central bore and a hub slidably coupled thereto; a plurality of drive wires operatively coupled to the hub, each drive wire being configured and adapted to be received in a respective longitudinal channel and having a distal end terminating in a tip configured and adapted to be received in a respective radially angled channel of the body; and a cover slidably disposed about the body and the pusher; plurality of needle anchors configured and adapted to be seated within a respective one of the radially angled channels of the body, each needle anchor being provided with means for coupling to a distal end of a respective drive wire; and a plurality of sutures, wherein suture is secured to an outer surface of a respective needle anchor, threaded through the openings holes formed in the flange of the anchor fitting, through the collar of the anchor fitting and anchored to an inner surface of the cartridge.

These and other objects, along with advantages and features of the present invention herein disclosed, will become apparent through reference to the following description of embodiments of the invention, the accompanying drawings, and the claims.

BRIEF DESCRIPTION OF THE DRAWINGS

The accompanying drawings, which are incorporated in and constitute a part of this specification, illustrate embodiments of the invention and, together with the general description of the invention given above, and the detailed description of the embodiments given below, serve to explain the principles of the invention.

FIG. 10 is an enlarged perspective view of the insert of the device in accordance with the present disclosure;

FIG. 11 is an enlarged perspective view of the body of the device in accordance with the present disclosure;

DETAILED DESCRIPTION OF PREFERRED EMBODIMENTS

Figure 1:
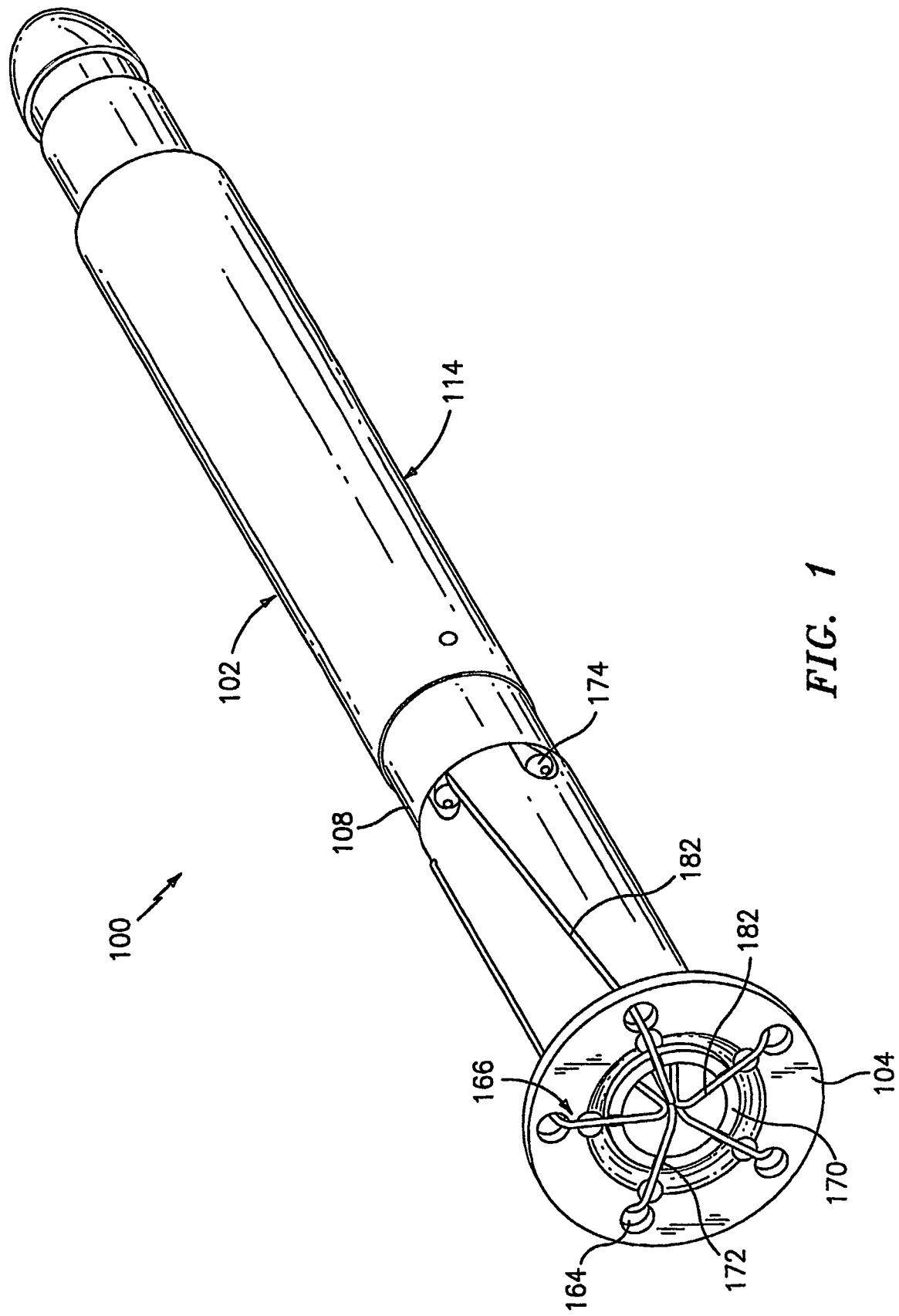
FIG. 1 is an enlarged perspective view of a radical prostatectomy anastomosis device in accordance with the present disclosure, as seen from a distal end thereof.
Figure 2:
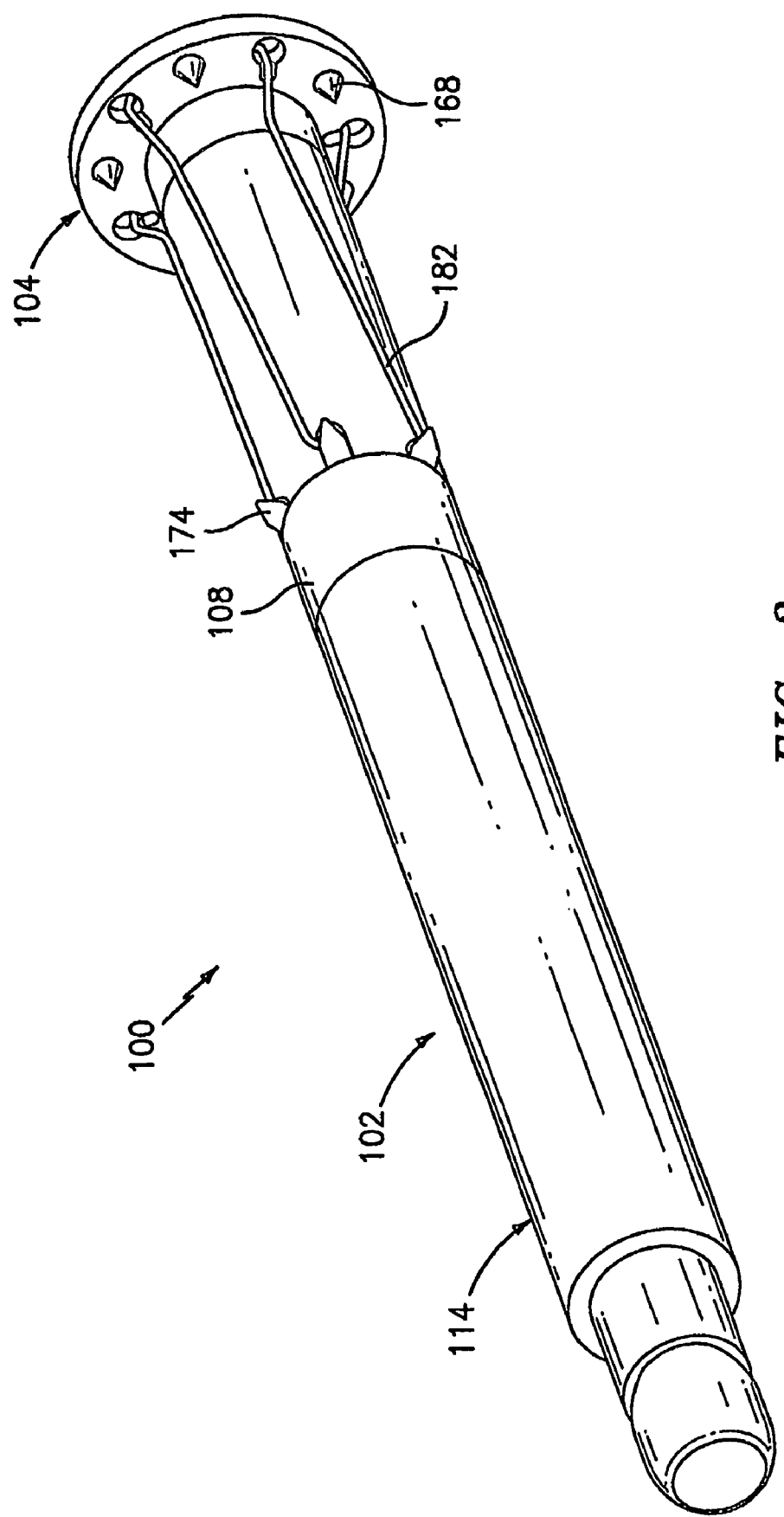
FIG. 2 is an enlarged perspective view of the device of FIG. 1, as seen from a proximal end thereof.
Figure 3:
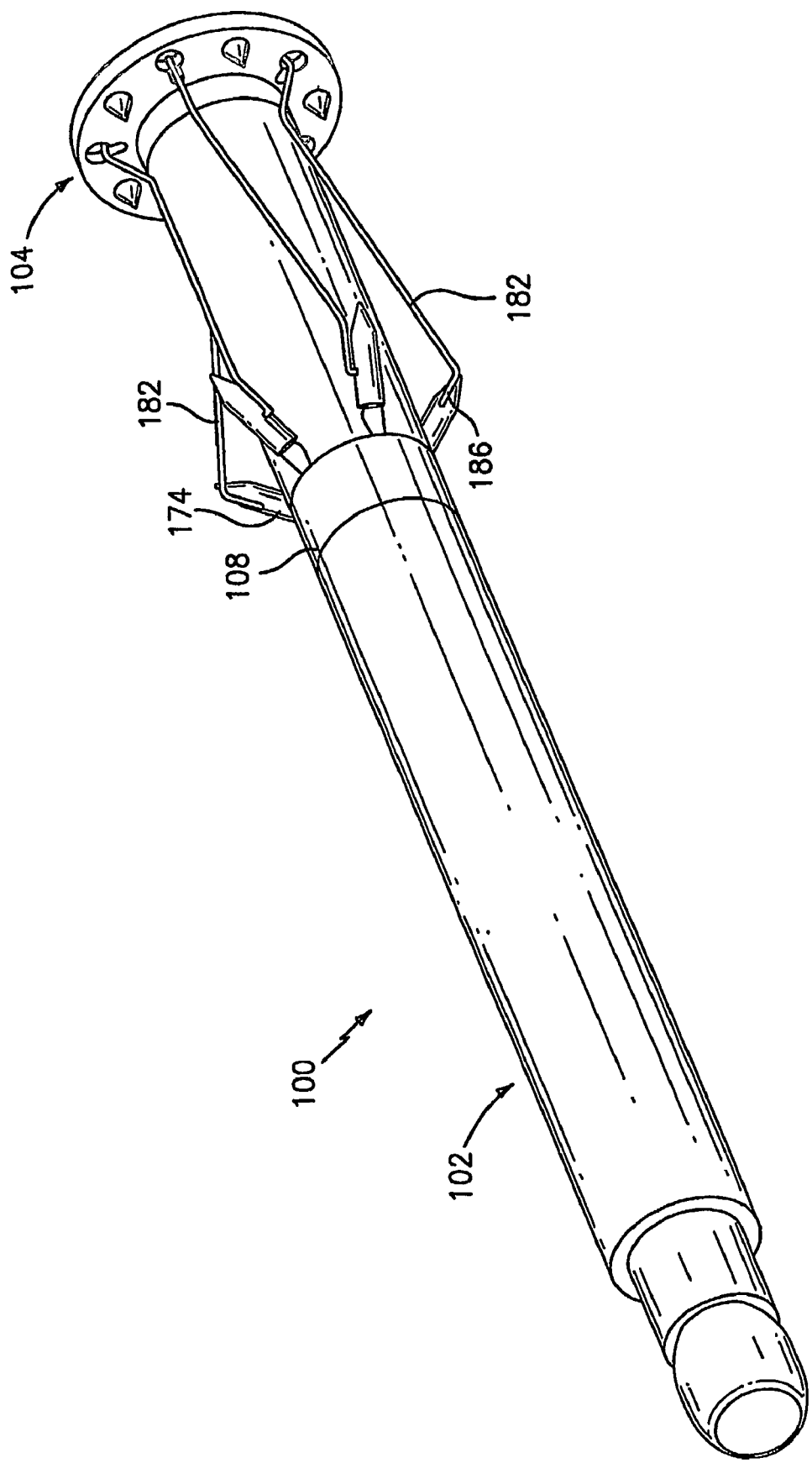
FIG. 3 is an enlarged perspective view of the device as shown in FIG. 2, with anchors fired radially outward from the cartridge body.

Preferred embodiments of the presently disclosed radical prostatectomy anastomosis device will now be described in detail with reference to the drawing figures wherein like reference numerals identify similar or identical elements.

Referring now to FIGS. 1-12, an anastomosis device, in accordance with the present disclosure, is generally shown as 100. Although device 100 offers significant advantages to a radical prostatectomy procedure, it will be understood that the device is applicable for use in any anastomosis procedure where two body vessels are to be joined to one another, such as where the end of a conduit is to be sutured to a hollow body organ. Device 100 includes a tubular cartridge 102 and a fitting 104 operatively coupled to a distal end of tubular cartridge 102.

As seen in FIGS. 5-12, tubular cartridge 102 includes a body 106, an insert collar 108 operatively coupled to body 106, a pusher sub-assembly 110 slidably coupled to body 106, a compression spring 112 disposed about body 106 and pusher sub-assembly 110 and a cover 114.

Figure 14:
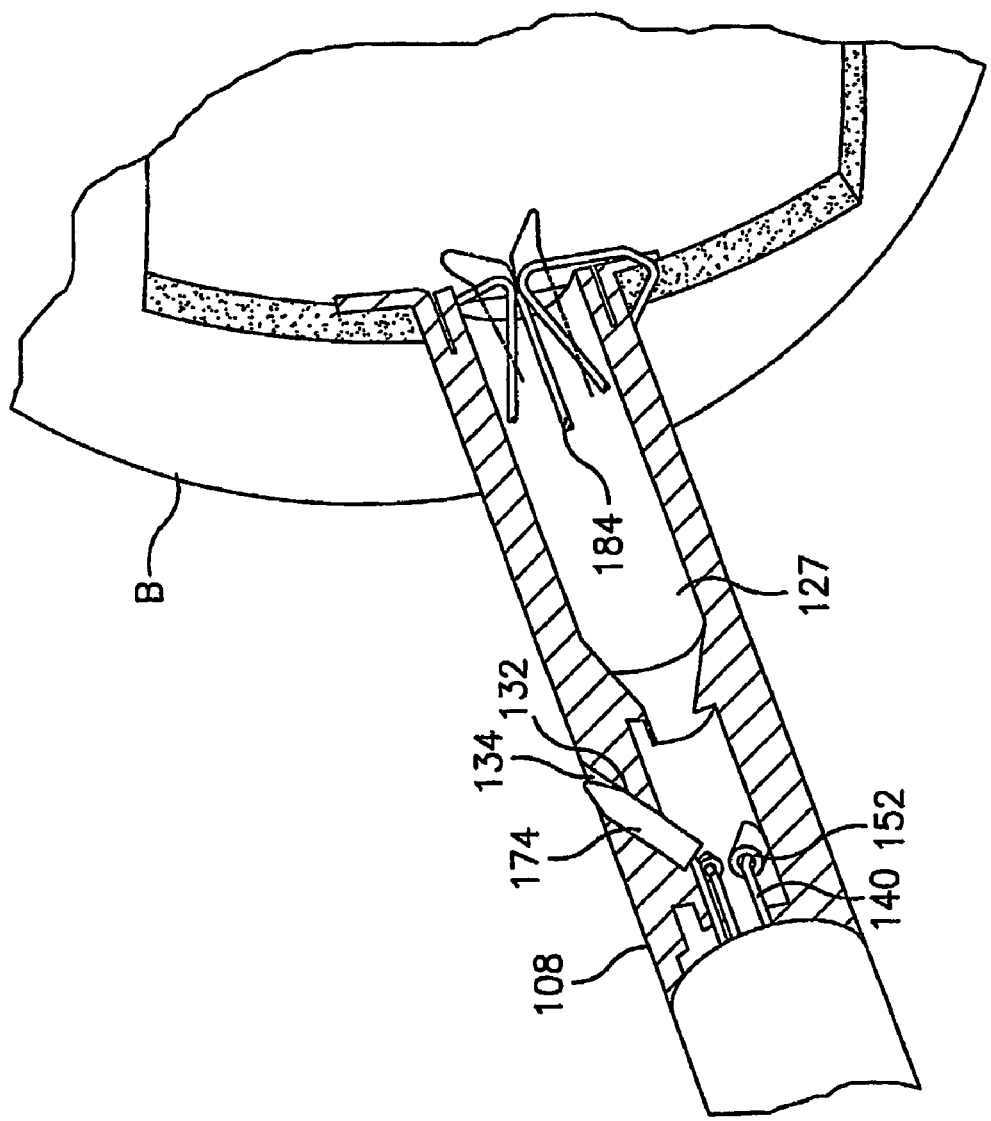
FIG. 14 is a partial section view of the device of the present disclosure inserted into the bladder neck.

As seen in FIG. 11, body 106 includes a central shaft 116 having a first cylindrical portion 118 formed at a distal end thereof having a diameter larger than shaft 116 thereby defining a first shoulder 120 therebetween, a second cylindrical portion 122 formed distally of first cylindrical portion 118 and having a diameter larger than first cylindrical portion 118 thereby defining a second shoulder 124 therebetween, a third cylindrical portion 126 formed distally of second cylindrical portion 122 and having a diameter larger than second cylindrical portion 122 thereby defining a third shoulder 128 therebetween, and a fourth cylindrical portion 129 formed distally of third cylindrical portion 126 and having a diameter smaller than third cylindrical portion 126. Body 106 includes an axial bore 127 formed in a proximal end thereof (see FIG. 14).

Body 106 is provided with a plurality of radially extending channels 130 extending along the length of central shaft 116 and terminating in angled channels 132 extending through first, second and third cylindrical portions 118, 122 and 126 respectively and defining openings 134 radially around a proximal end of third cylindrical portion 126. Preferably, body 106 is provided with five channels 130, although it is envisioned that any number of channels can be provided.

Insert collar 108 has an outer diameter substantially equal to the diameter of third cylindrical portion 126 and an inner diameter slightly larger than the diameter of second body portion 122. In this manner, collar 108 is slidably received about second body portion 122 (see FIG. 8). Collar 108 includes a plurality of teeth 136 extending radially inward from an inner surface thereof. Preferably, collar 108 is provided with an equal number of teeth 136 as channels 130 (i.e., in the present embodiment five as seen in FIG. 10). Teeth 136 are configured and adapted to compliment and enclose angled channels 132 thereby defining a passage therethrough. While a two piece assembly of body 106 and collar 108 has been disclosed, it is envisioned that the body and collar can be formed from one unitary piece having a plurality of passages machined or molded therein. However, in order to reduce the cost of manufacture, body 106 and collar 108 have been separately formed and later assembled.

Figure 12:
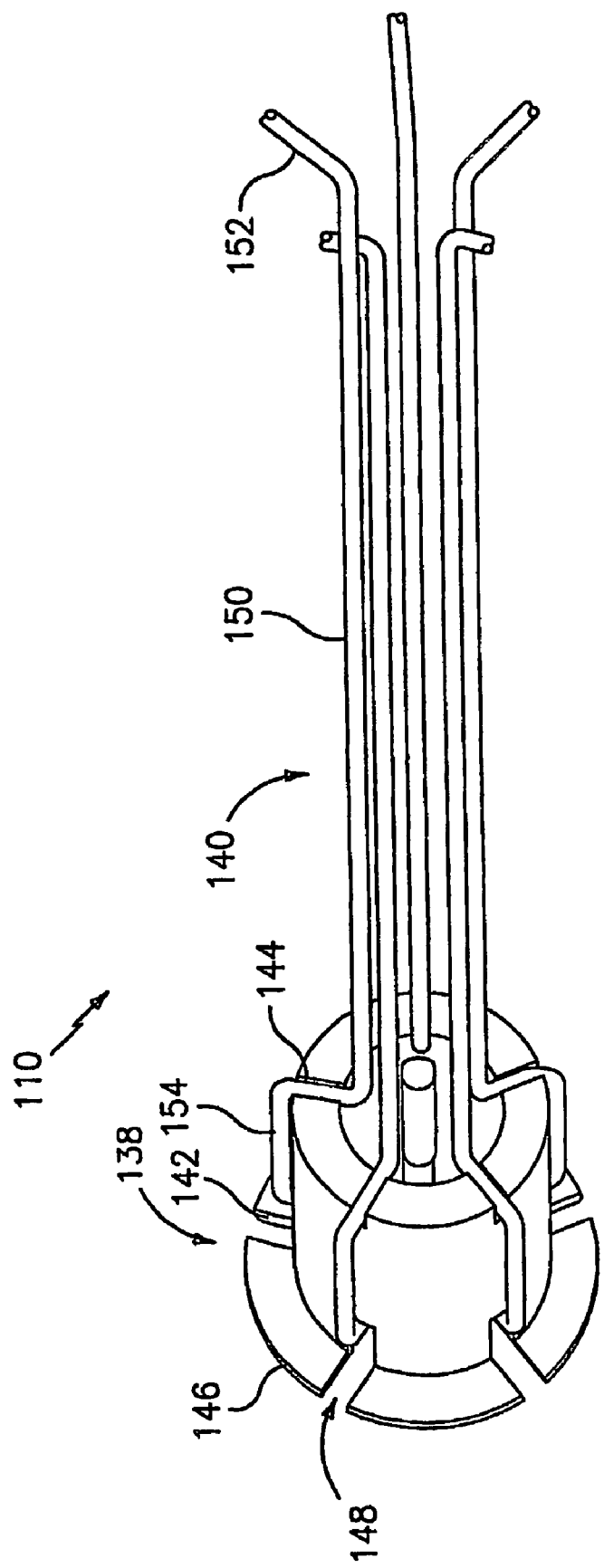
FIG. 12 is an enlarged perspective view of the pusher sub-assembly of the device in accordance with the present disclosure.

Turning now to FIG. 12, pusher sub-assembly 110 includes a hub 138 having a plurality of drive wires 140 operatively coupled thereto. Hub 138 includes a hollow cylindrical body portion 142 having a plurality of radially extending slots 144 formed is a distal end thereof and a flange 146 having a plurality of radially extending slots 148, radially aligned with slots 144, formed at a proximal end thereof. Hub 138 has an inner diameter slightly larger than the diameter of central shaft 116 of body 106 and an outer diameter substantially equal to the diameter of first cylindrical portion 118 of body 106. Hub 138 is slidingly received on central shaft 116.

Each drive wire 140 includes a body portion 150 receivable in channels 130 of shaft 116, a distal end 152 configured and adapted to be received within angled channels 132 of body 106 and a proximal end 154 configured and adapted to be received in slots 144 and 148 of hub 138. In this manner, as hub 138 is moved distally along central shaft 116, each drive wire 140 is moved distally, and as hub 138 is moved proximally along central shaft 116 each drive wire 140 is moved proximally as well. The length of body portion 150 of each drive wire 140 is such that when pusher sub-assembly 110 is coupled to body 106, a proximal tip of central shaft 116 extends proximally from hub 138. (See FIGS. 5, 7 and 8) Preferably, there are an equal number of drive wires 140 as there are channels 130.

Figure 7:
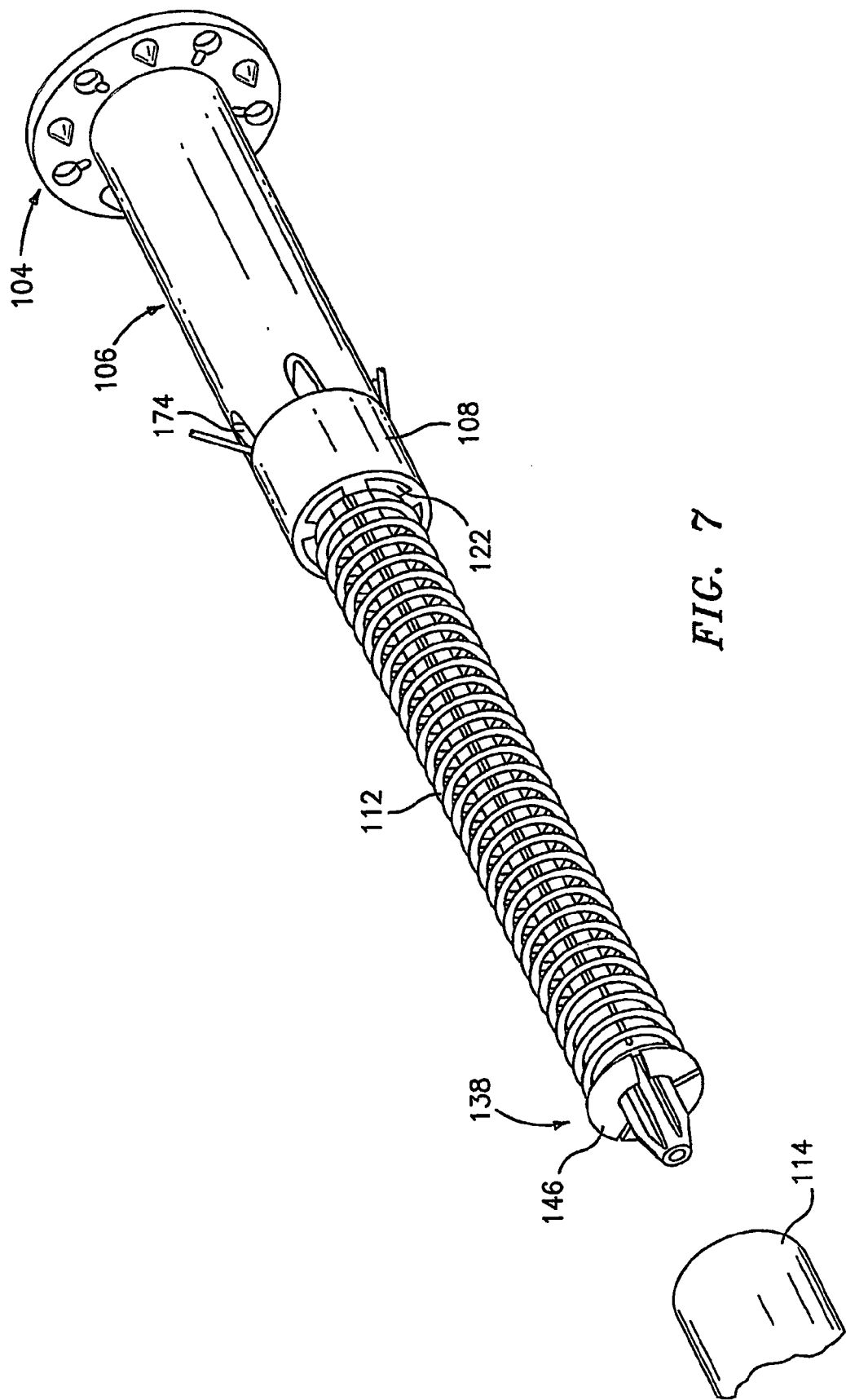
FIG. 7 is an enlarged partially exploded perspective view of the device as shown in FIG. 2 with the cover tube removed therefrom.
Figure 8:
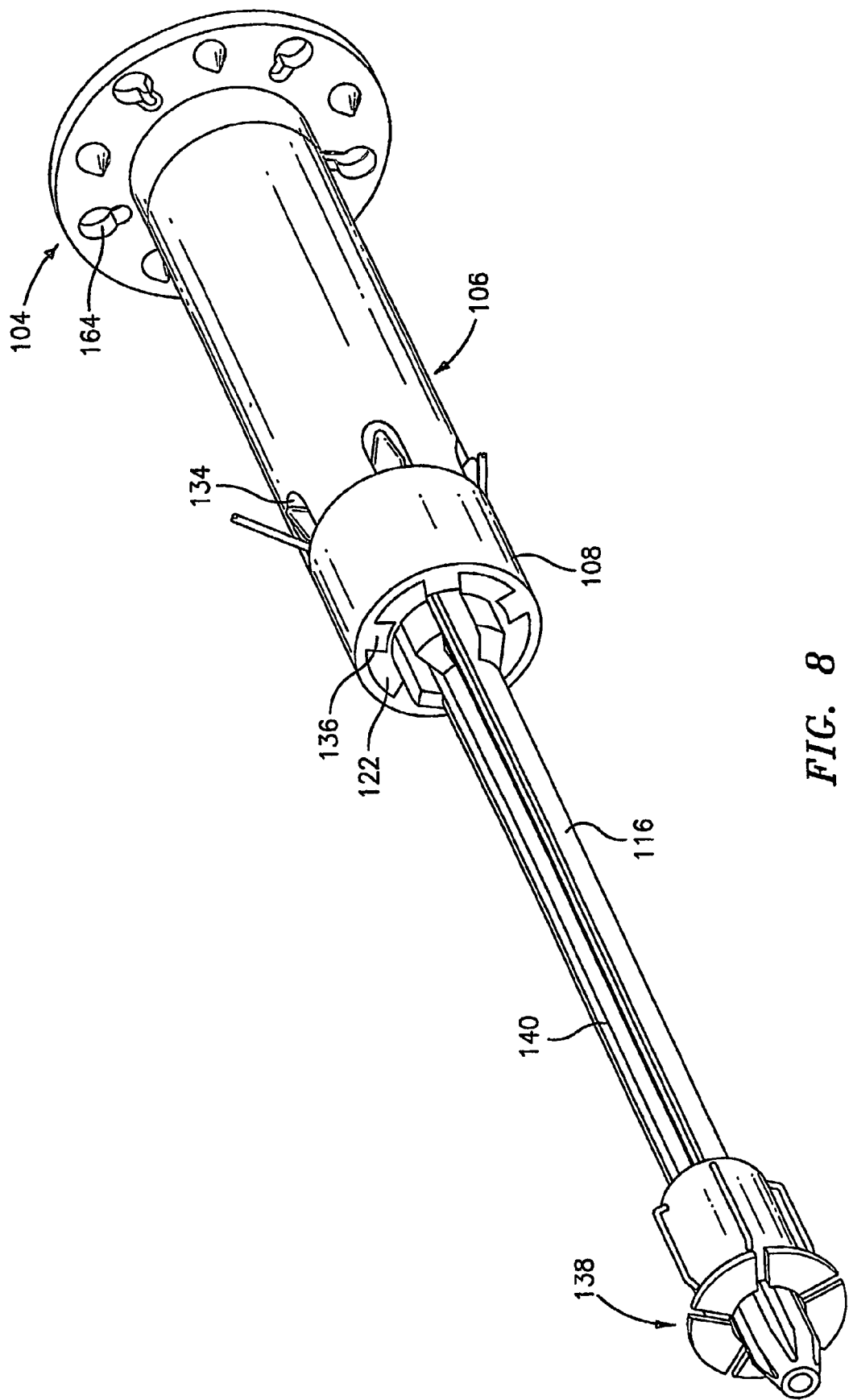
FIG. 8 is an enlarged partially exploded perspective view of the device as shown in FIG. 7 with the return spring removed therefrom.
Figure 9:
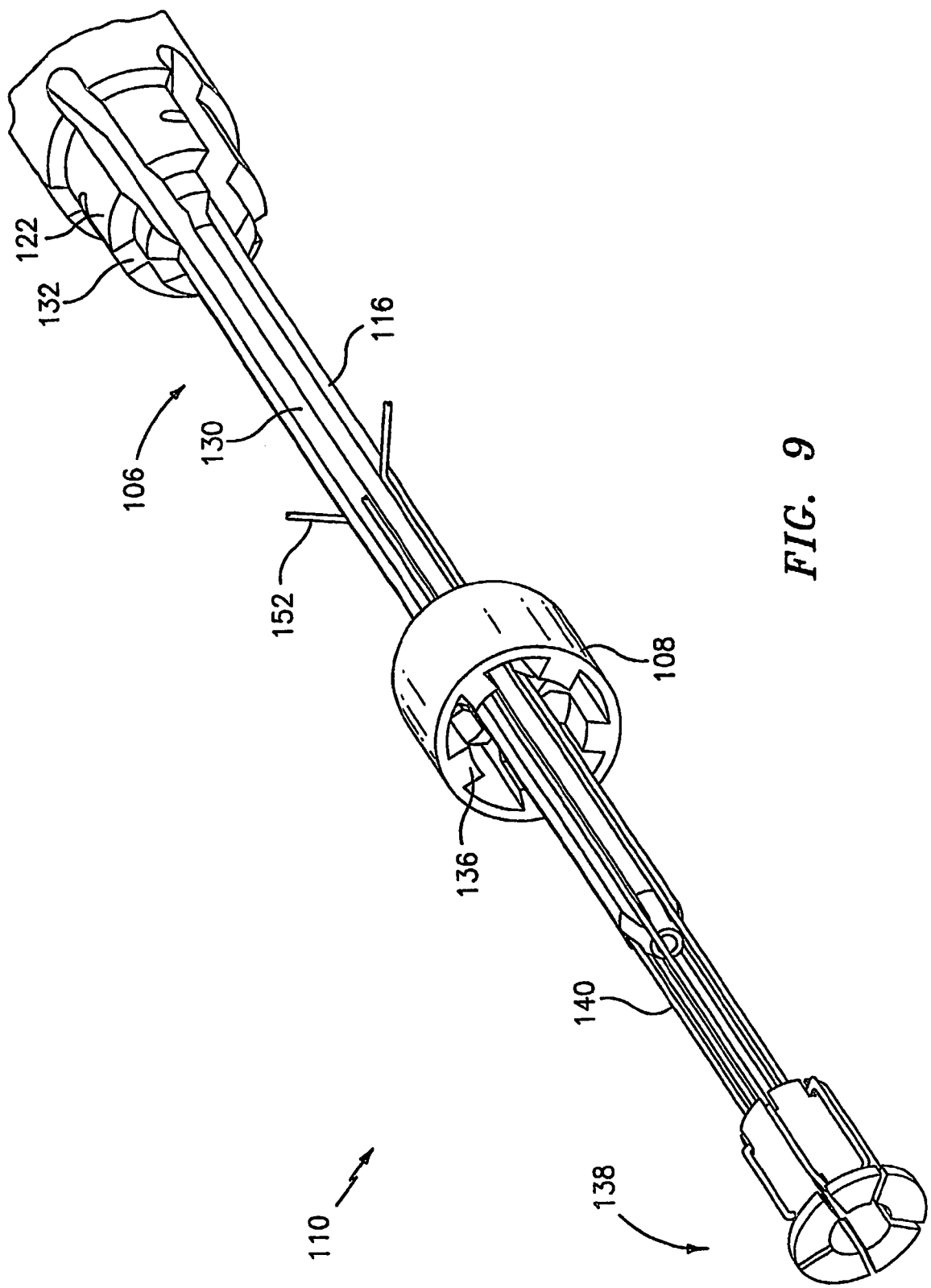
FIG. 9 is an enlarged partially exploded perspective view of the interaction of the body, the pusher sub-assembly and the insert collar of the device in accordance with the present disclosure.

Assembly of cartridge 102 is best described with reference to FIGS. 7-9. As seen in FIGS. 8 and 9, shaft 116 of body 106 is inserted through collar 108, drive wires 140 are then aligned with channels 130 and fed between shaft 116 and collar 108 until distal ends 152 are received within angled channels 132 of body 106, and then teeth 136 of collar 108 are aligned with angled channels 132 such that hub 138 is seated over second cylindrical body portion 122. Accordingly, as hub 138 moves distally along shaft 116, drive wires 140 will project outwardly from holes 134. Preferably drive wires 140 are made from a semi-deformable material (i.e., copper) which is rigid yet pliable thereby allowing body portion 150 of drive wire 140 to curve and bend through angled channel 132 as hub 138 is moved distally. In other words, drive wires 140 are movable through angled channel 132 by operation of hub 138. Accordingly, each drive wire 140 includes portions which are sufficiently flexible to negotiate the transition between angled channel 132 and As seen in FIG. 7, compression spring 112 is disposed about hub 138 and first cylindrical portion 118 of body 106 between flange 146 of hub 138 and second cylindrical body portion 122. In this manner, as hub 138 is depressed distally along shaft 116, flange 146 presses against a proximal end of spring 112 causing spring 112 to compress between flange 146 and second cylindrical portion 122 and become spring biased. Once the depression force acting on hub 138 is removed, the spring bias will cause spring 112 to expand and move hub 138 proximally to its original position.

Turning now to FIGS. 1-8, fitting 104 includes an annular sleeve 160 having a flange 162 extending radially outward from a distal end thereof. Annular sleeve 160 has an inner diameter slightly larger than the outer diameter of fourth cylindrical portion 129 of body 106 and an outer diameter substantially equal to the outer diameter of third cylindrical portion 126 of body 106. In this manner, annular sleeve 160 of fitting 104 is slidably received on fourth cylindrical portion 129 such that there is a smooth transition from the outer surface of annular sleeve 160 to third cylindrical portion 126.

Fitting 104 includes a plurality of holes 164 formed through flange 162. Preferably, there are an equal number of holes 164 as there are channels 130 and/or drive wires 140, namely, five in the present disclosure. Each hole 164 is desirably provided with suture locking means 166 which is configured and adapted to frictionally grab on to and hold a suture that has been press fit therein (as will be described further below). Fitting 104 further desirably includes a plurality of anchors 168, integrally formed with and extending proximally from a proximal surface of flange 162. It is envisioned that anchors 168 can be any shape (i.e., conical, pyramidal, barbs, pointed and the like). As seen in FIG. 1, fitting 104 includes an annular rim 170 being co-axial with annular sleeve 160 and projecting axially from a distal surface of flange 162. Annular rim 170 also preferably includes a plurality of grooves 172 formed along a distal surface thereof and being radially aligned with holes 164 of flange 162.

Fitting 104 can be made from any surgical grade material, however, fitting 104 is preferably made from medical grade bio-absorbable materials, such as, for example, Polyglycolic Acid (PGA) and Polylactic Acid (PLA). Preferably, fitting 104 provides sufficient strength to retain a body vessel open and anchored thereto for a desired period of time to enable proper healing of the first body vessel to the second body vessel, after which, the fitting can be absorbed into or passed out of the body.

Anastomosis device 100 further includes a plurality of bio-absorbable anchors 174. Anchors 174 include a body portion 176 having a shaped distal tip 178 to facilitate penetration of body tissue and desirably include a recess 180 formed in a proximal surface thereof (see FIG. 4). Anchors 174 are slidably disposed in angled channels 132 such that an anchor 174 is seated on distal end 152 of each drive wire 140 and such that tip 178 is oriented to be radially expelled from opening 134 of angled channels 132. The recesses 180 may be provided for seating the anchors 174 on the drive wires 140. Anchors 174 can be made from any surgical grade material (i.e., stainless steel, titanium, etc.), however, anchors 174 are preferably made from medical grade bio-absorbable materials, such as, for example, Polyglycolic Acid (PGA) and Polylactic Acid (PLA). Anchors 174 are of sufficient strength to be retained in a body vessel and to retain a first body vessel in contact with a second body vessel for a sufficient period of time to permit proper healing after which the anchors can be absorbed into the body.

Figure 4:
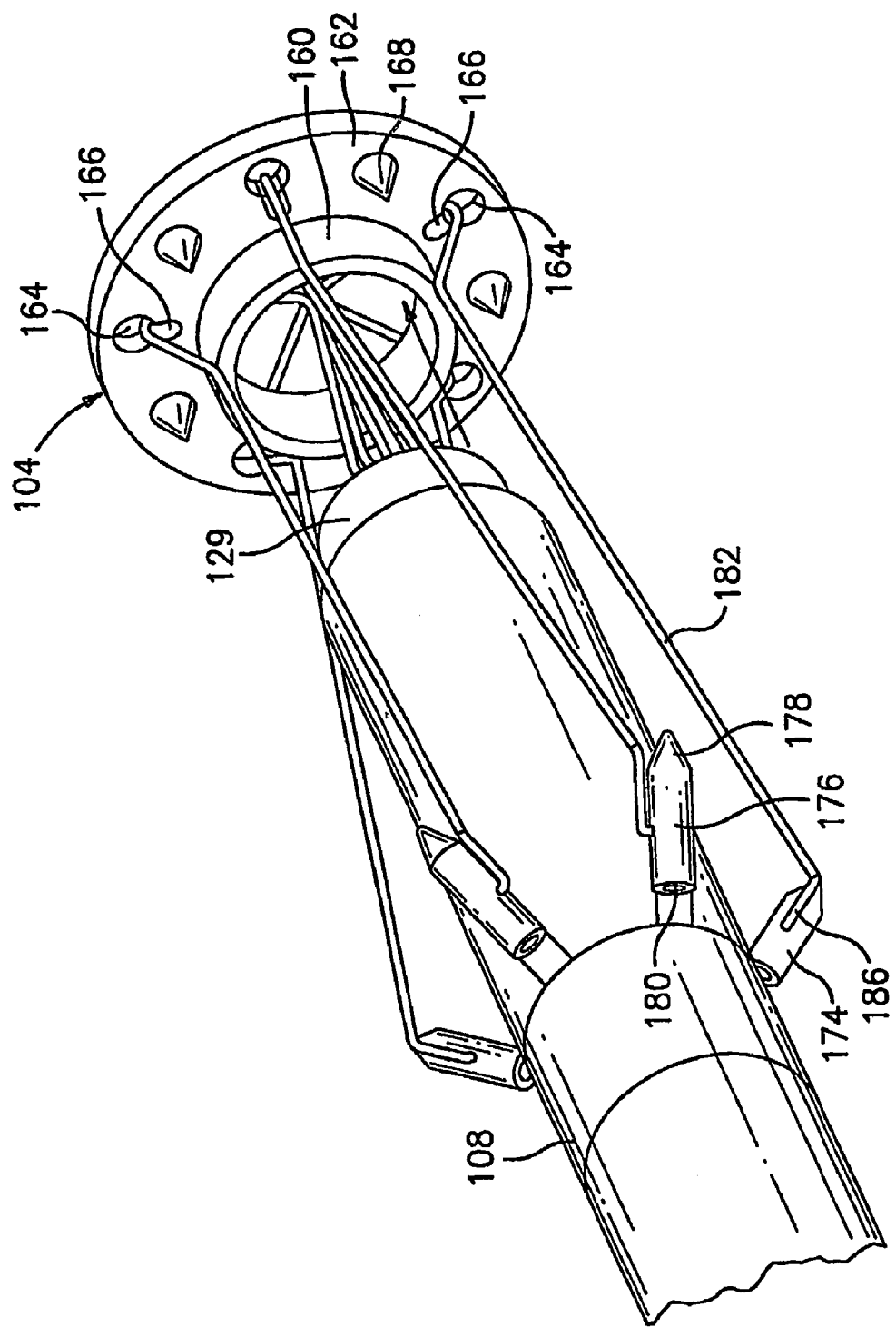
FIG. 4 is an enlarged partially exploded perspective view of the device as shown in FIG. 3, partially broken away, with the fitting separated from the cartridge body.

Anastomosis device 100 further includes a plurality of bio-absorbable sutures 182. As D seen in FIGS. 1-4 and 14, sutures 182 have a distal end 184 anchored to the inner surface of axial bore 127 of cartridge body 106 (see FIG. 14) and a proximal end 186 anchored to the outer surface of body portion 176 of anchors 174. With particular reference to FIGS. 1 and 4, sutures 182 are passed out of axial bore 127, placed in groove 172 of rim 170 of fitting 104, through hole 164 of flange 162 of fitting 104 and into hole 134 of angled channel 132 to the outer surface of body portion 176 of anchor 174. Sutures 182 can be made from any surgical grade material, however, sutures 182 are preferably made from medical grade bio-absorbable materials, such as, for example, Polyglycolic Acid (PGA) and Polylactic Acid (PLA). The anchors need to be of sufficient strength to retain the first body vessel in contact with the second body vessel for a sufficient period of time to allow for proper healing after which the sutures can be absorbed into the body. In a preferred method, it is contemplated that fitting 104, anchors 174 and sutures 182 maintain their integrity for a period of at least two weeks in order for the first body vessel to naturally adhere to the second body vessel, such as the bladder and urethra.

Figure 5:
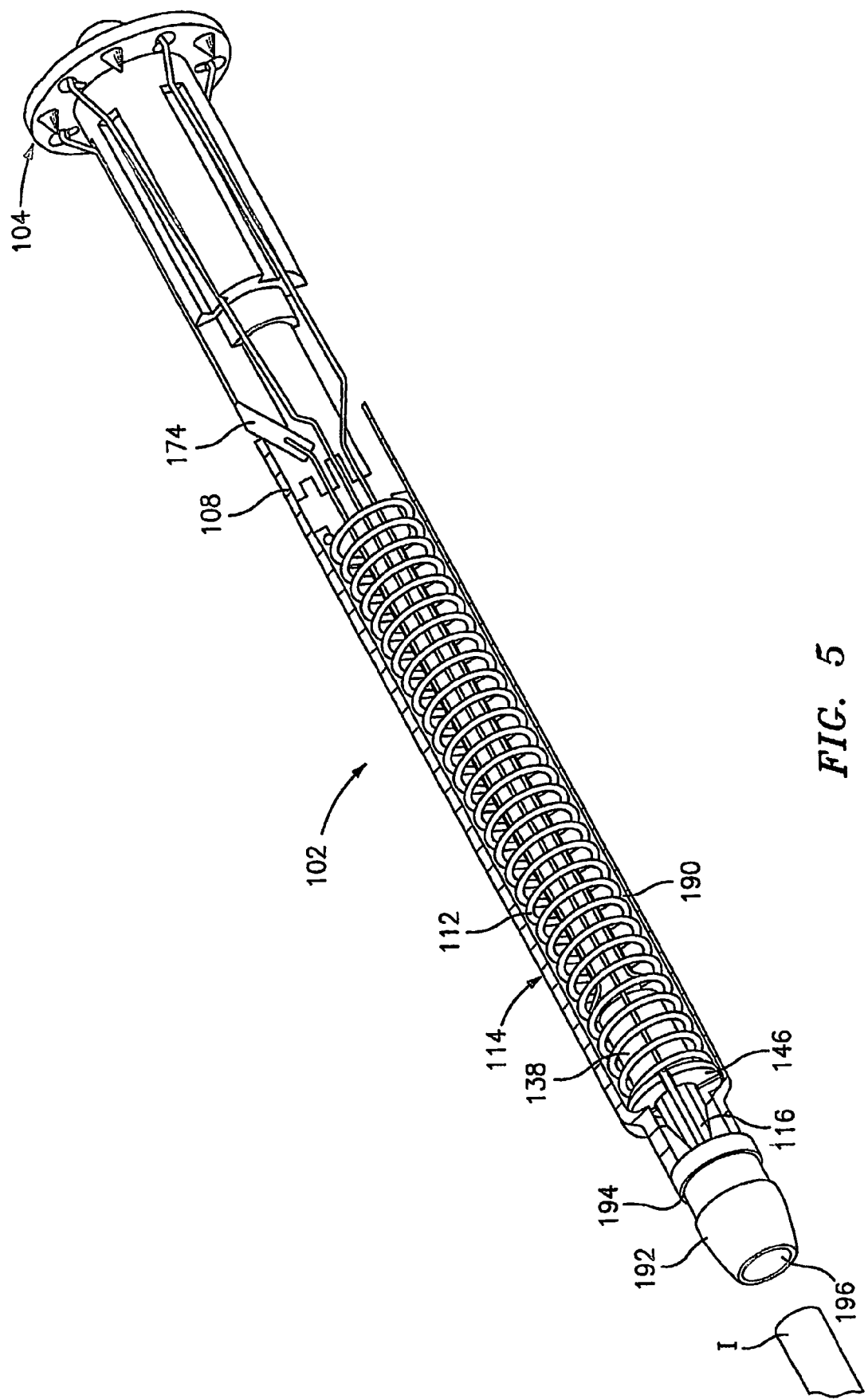
FIG. 5 is an enlarged partial cross-section perspective view of the device as shown in FIG. 2.
Figure 6:
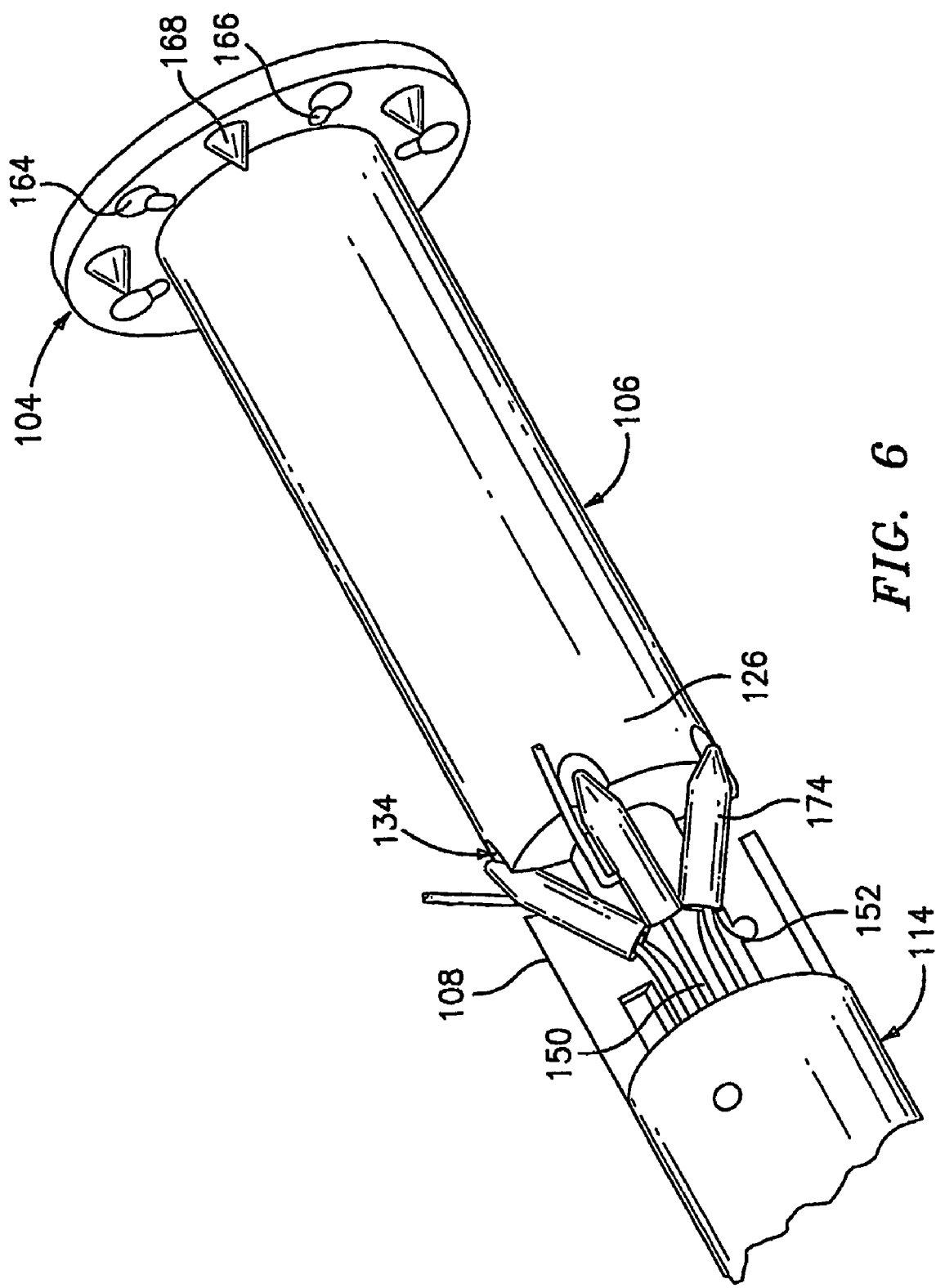
FIG. 6 is an enlarged partial cross-section perspective view of the device as shown in FIG. 2, with the insert collar partially broken away.
Figure 15:
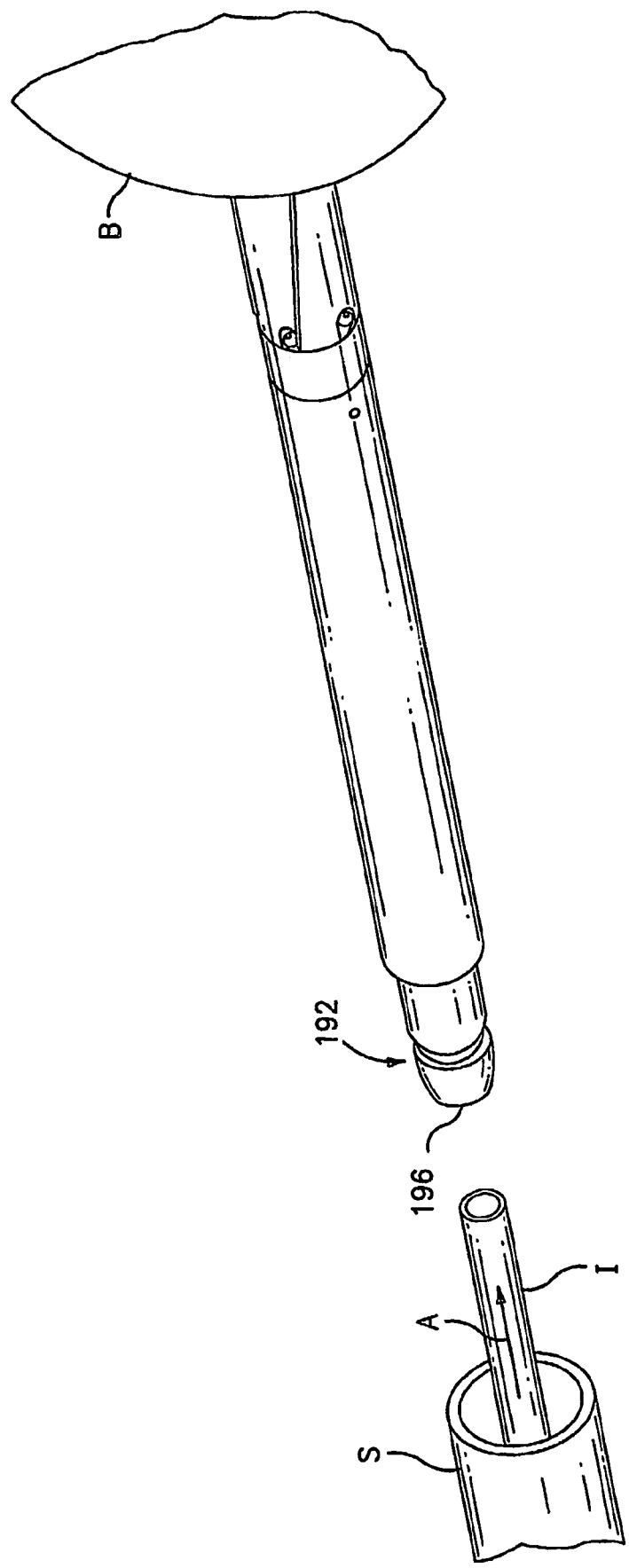
FIG. 15 is a perspective view of the device, of the present disclosure, after insertion into the bladder neck of the bladder and prior to engaging the surgical instrument and the urethral stump of the patient.

As seen in FIG. 5, cartridge 102 includes cover 114 having a hollow body portion 190 and a head 192 formed at a proximal end thereof. Hollow body portion 190 has an outer diameter substantially equal to the outer diameter of collar 108, which body portion 190 is configured and adapted to abut the proximal surface of collar 108 and enclose spring 112, pusher sub-assembly 110 and central shaft 116 of body 106 therein. Head 192 has a diameter smaller than body portion 190, thereby defining a shoulder 194, and an inner diameter larger than the diameter of central shaft 116 to thereby receive the proximal tip of central shaft 116 therein. When cover 114 is in place, flange 146 of hub 138 abuts against shoulder 194. Head 192 is provided with an axial central bore 196 for receiving a surgical instrument "I" therein and has an outer surface shaped to be readily received in a body vessel, such as the distal end of a urethral stump. As seen in FIGS. 5 and 15, instrument "I" is generally a hollow tube having an outer diameter smaller than the inner diameter of axial bore 196 of head 192 and an inner diameter slightly larger than the outer diameter of central shaft 116 of body 106.

In use, instrument "I" is inserted through axial bore 196 of head 192 and over the proximal end of central shaft 116 until the distal end of instrument "I" abuts against the proximal surface of flange 146 of hub 138. By pressing instrument "I" distally into cartridge 102, hub 138 advances drive wires 140 forward and ultimately anchors 170 radially outward from cartridge 102, thereby imbedding anchors 170 into the body vessel, such as urethral stump "U" (See FIG. 19). When instrument "I" is pressed into cartridge 102, it is envisioned that the outer surface of instrument "I" snap fits into cartridge 102 such that cartridge 102 can be selectively released from instrument "I" as needed. In other embodiments, the instrument has a control member accessible at a proximal end of the instrument and arranged to cooperate with the cartridge 102 for deploying the anchors 170. The instrument may have other configurations and the pusher assembly 110 may have other arrangements. For example, the anchors 170 may be spring loaded in openings 134 and released by a latch at the proximal end of the instrument. It is contemplated that the pusher assembly 110 may have other arrangements.

Use and operation of anastomosis device 100 in performing a radical prostatectomy anastomosis will now be described in greater detail with reference to FIGS. 1-20 and in particular with reference to FIGS. 13-20. Device 100 can be used in either the retropubic or the perineal prostatectomy approaches, laparoscopic or any other approaches. With the prostate removed, the bladder neck "N" of the bladder "B" is first reconstructed by everting the inner mucosal lining of the bladder "B" and suturing it down to the outer wall of the bladder "B".

Figure 13:
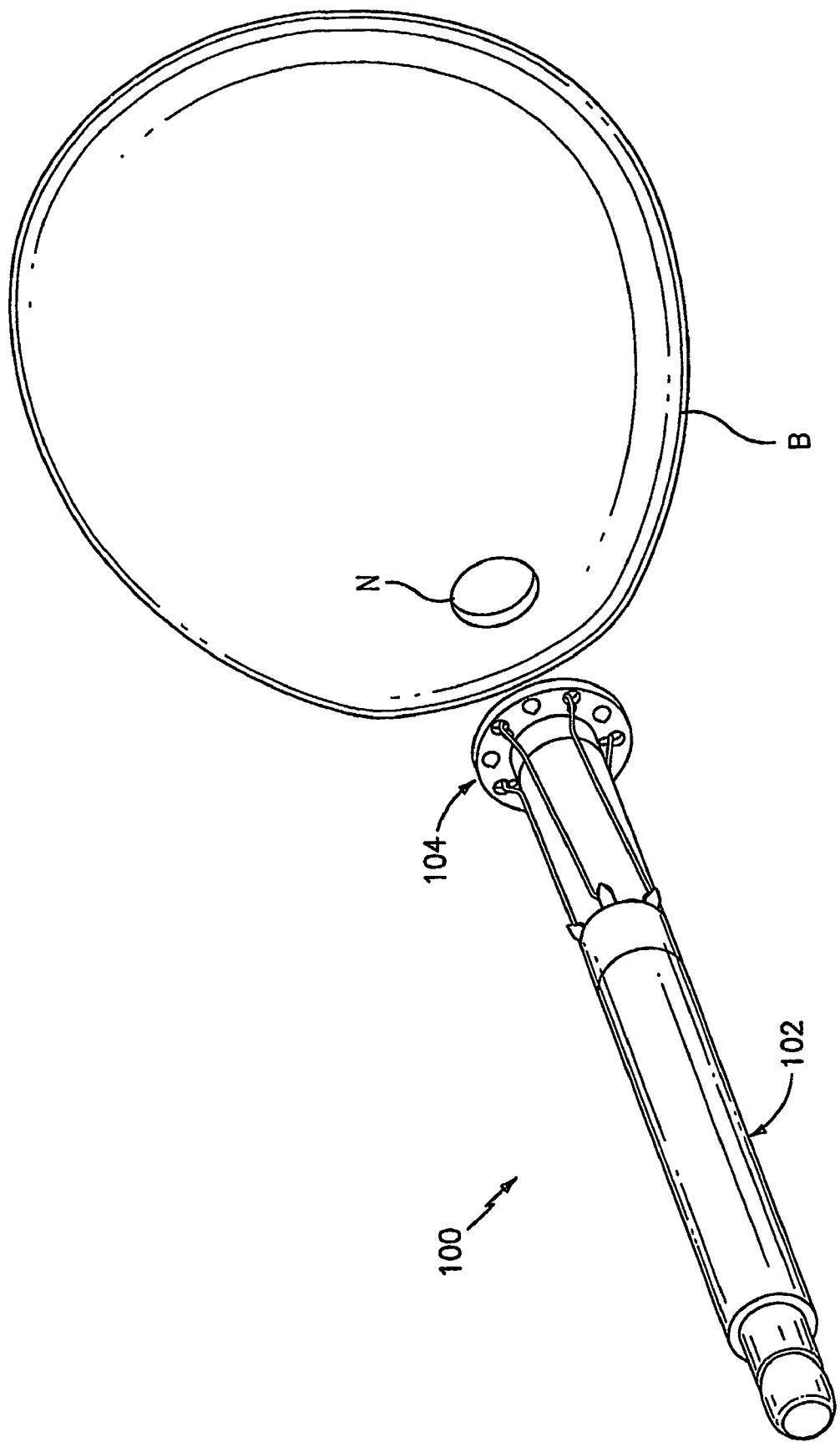
FIG. 13 is an illustration of the device of the present disclosure ready to be inserted into the bladder neck of a bladder of a patient.

As seen in FIG. 13, with the bladder neck "N" reconstructed, the bladder neck "N" is next sized to properly accommodate and retain fitting 104 within bladder "B" using a standard tennis racket type closure (i.e., the opening of the bladder neck constituting the head of the tennis racked and a radial incision extending from the bladder neck constituting the handle portion of the tennis racket). Flange 162 of fitting 104 is then inserted into the bladder "B" through the bladder neck "N" and the handle portion of the tennis racket closure sutured closed around annular sleeve 160 thereby preventing flange 162 of fitting 104 from being withdrawn from bladder neck "N" (see FIG. 14). Alternatively, bladder neck "N" can be sized to receive flange 162 of fitting 104 and a purse string suture used to constrict and cinch bladder neck "B" around annular sleeve 160.

Figure 16:
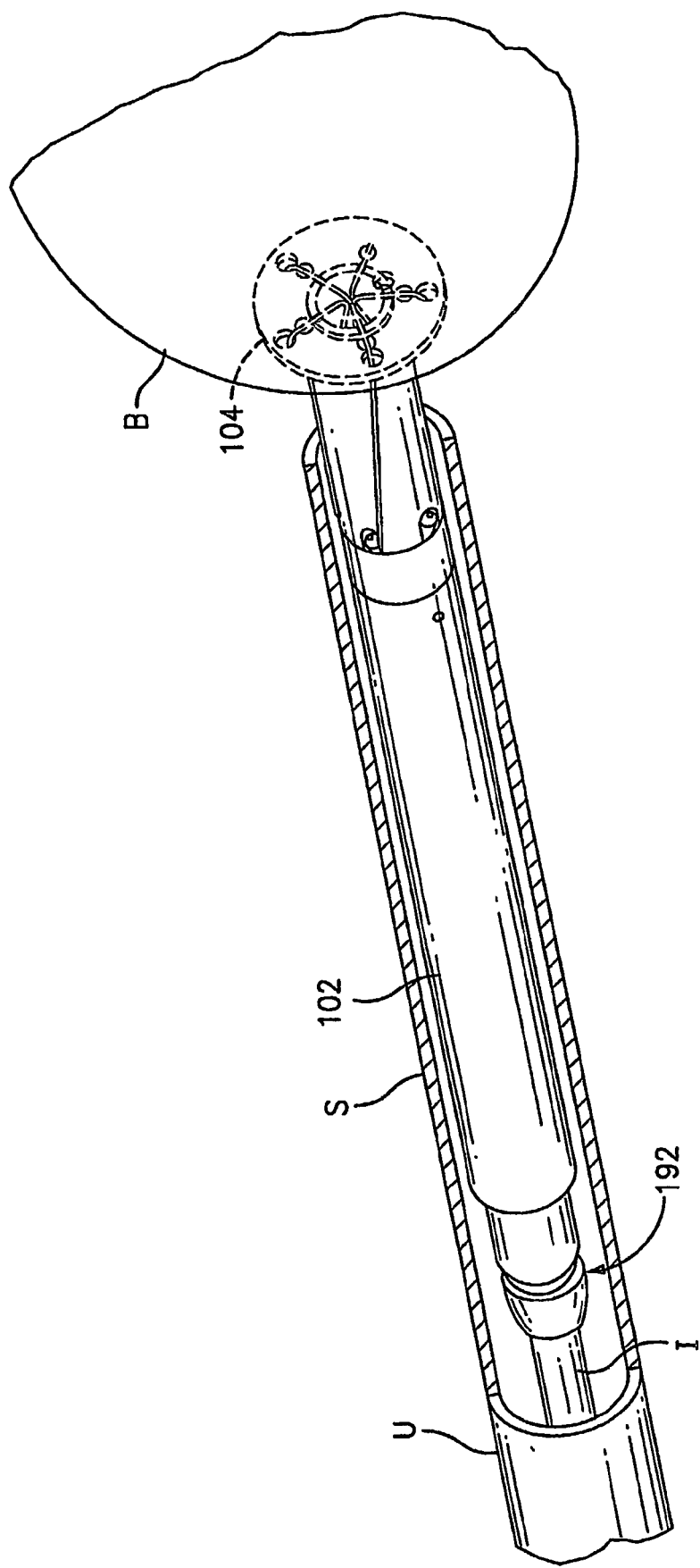
FIG. 16 is a perspective view of the device of the present disclosure ready to be drawn proximally through the urethral stump of a patient and prior to the firing of the anchors.
Figure 17:
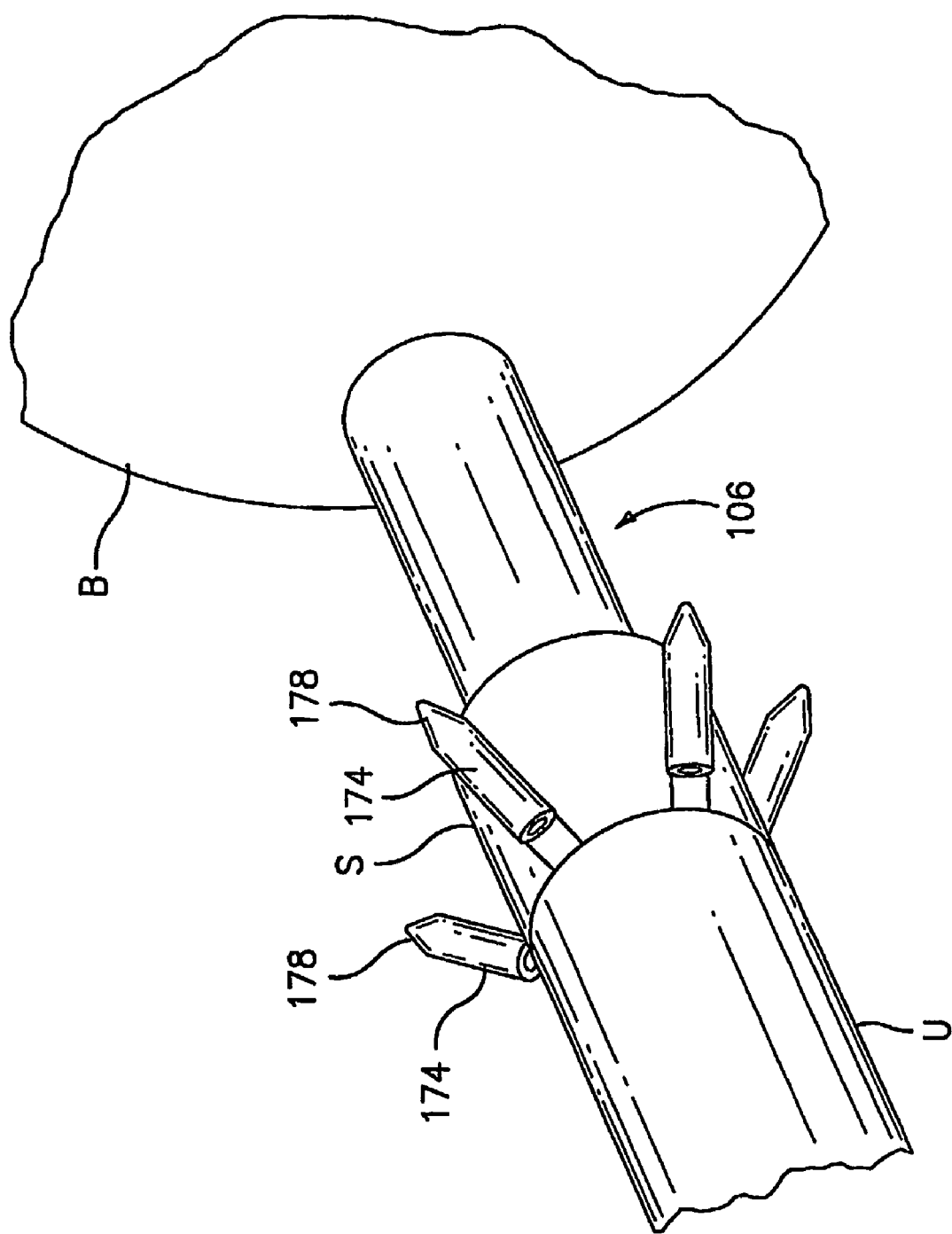
FIG. 17 is a perspective view of the device of the present disclosure with the anchors fired into and through the urethral stump of a patient.

With the distal end of device 100 secured to bladder neck "N", instrument "I" is passed trans-urethrally through urethra "U" and out through urethral stump "S" as indicated by arrow "A" (see FIG. 15). As seen in FIG. 16, the distal end of instrument "I" is then operatively coupled to the proximal end of device 100 such that instrument "I" is received within axial bore 196 of head 192 and over the proximal end of central shaft 116 until the distal end of instrument "I" abuts against the proximal surface of flange 146 of hub 138. Simultaneously, urethral stump "S" is slipped over the outer surface of head 192 and distally along the length of device 100 until the end of urethral stump "S" is positioned distal of holes 134 defined by angled channels 132 of body 106 and distal of anchors 174.

With urethral stump "S" in position around device 100, anchors 174 are deployed from channels 132 into and/or through the walls of urethral stump "S". Deployment of anchors 174 into urethral stump "S" includes distally advancing instrument "I" such that hub 138 advances drive wires 140 distally, thereby ejecting anchors 174, which are seated on distal ends 152 of drive wires 140 (see FIG. 14), radially outward from angled channels 132 of body 106 (see FIG. 17). The angle of channels 132 is such that distal tips 178 of anchors 174 advance toward bladder "B" thereby increasing the ability of anchors 174 to draw urethral stump "S" distally along device 100. In so doing, the proximal ends 186 of sutures 182, which are anchored to the outer surface of body portion 176 of anchors 174, are effectively stitched into urethral stump "S".

Generally, urethra "U" is prevented from movement by its attachment to the pelvic wall (not shown) and it is thus bladder "B" which is mobile or free to move toward urethra "U" in order to complete the anastomosis. Accordingly, turning now to FIG. 18, with anchors 174 imbedded into urethral stump "S", instrument "I" is withdrawn proximally through urethra "U". The withdrawal of instrument "I" releases fitting 104 from the distal end of cartridge 102 (i.e., fourth cylindrical portion 129 is withdrawn from annular sleeve 160). In so doing, sutures 182, which have their distal ends 184 anchored to the inner surface of axial bore 127 of cartridge body 106, are pulled proximally through fitting 104, thereby drawing proximal end 186 of sutures 182 and the attached urethral stump "S" distally along cartridge 102.

Figure 18:
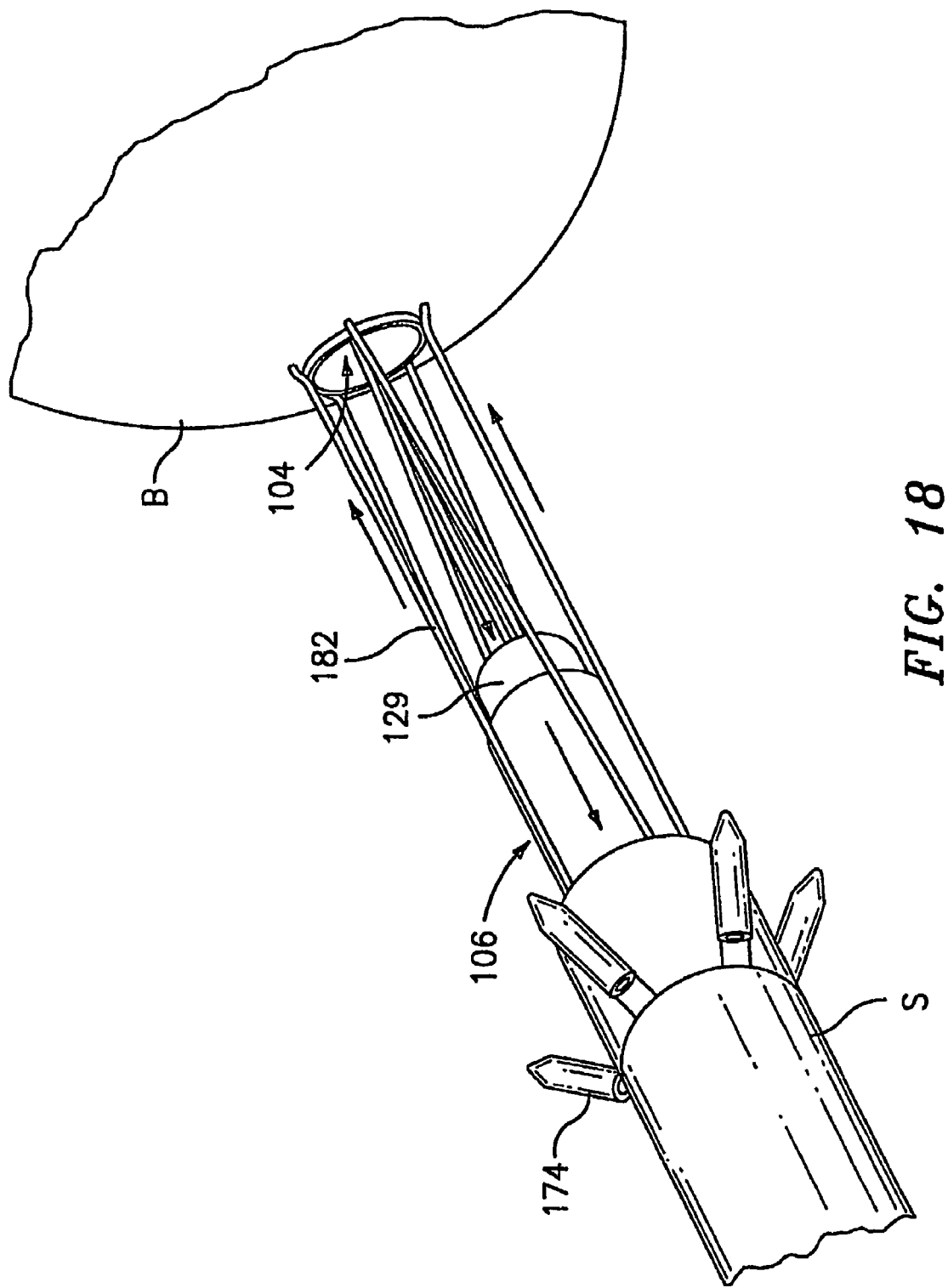
FIG. 18 is a perspective view of the device of the present disclosure being withdrawn proximally through the urethral stump.
Figure 19:
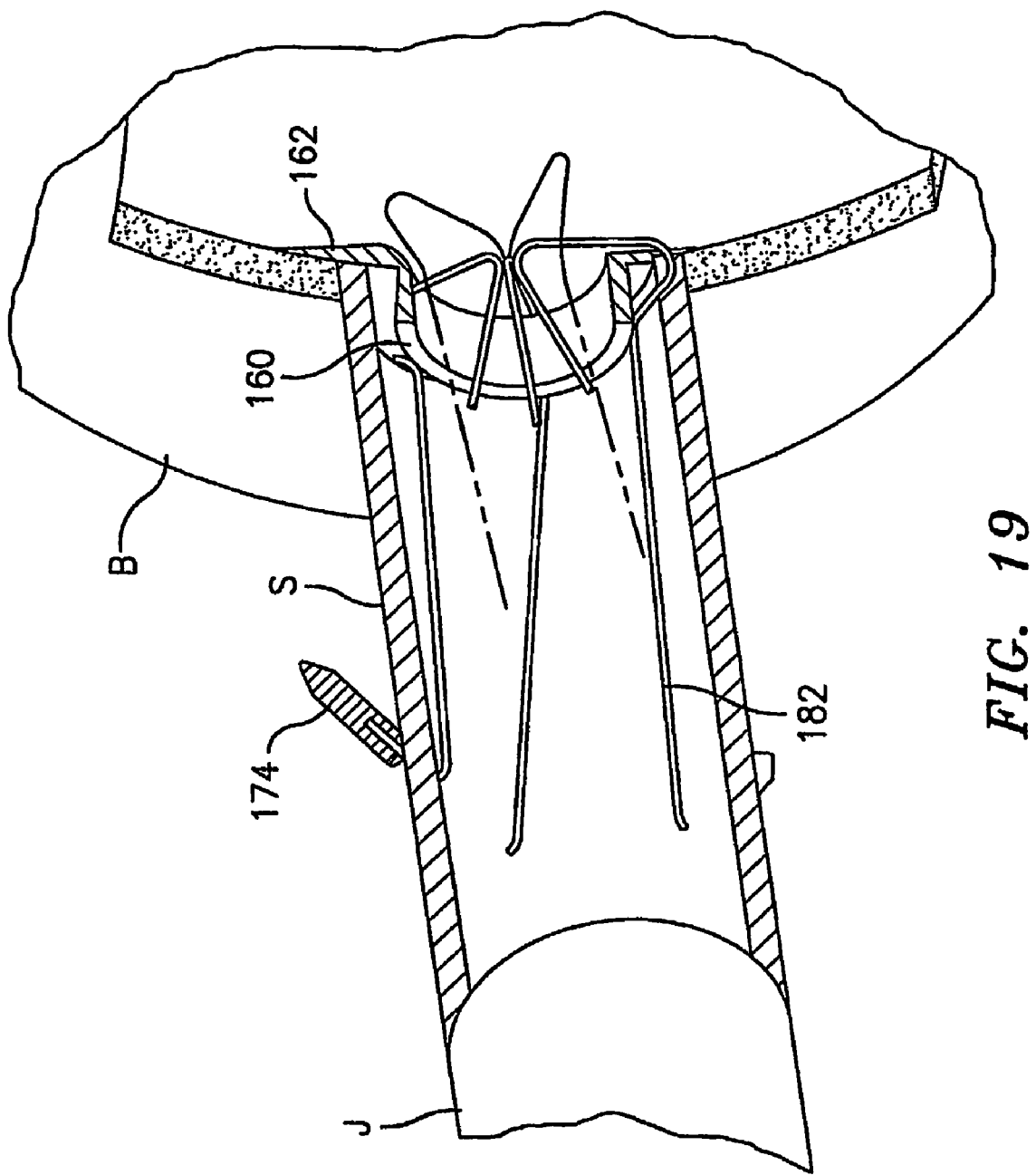
FIG. 19 is a cross-sectional perspective view of the device depicting the tightened anastomosis and shown with the distal end of the sutures cut free.
Figure 20:
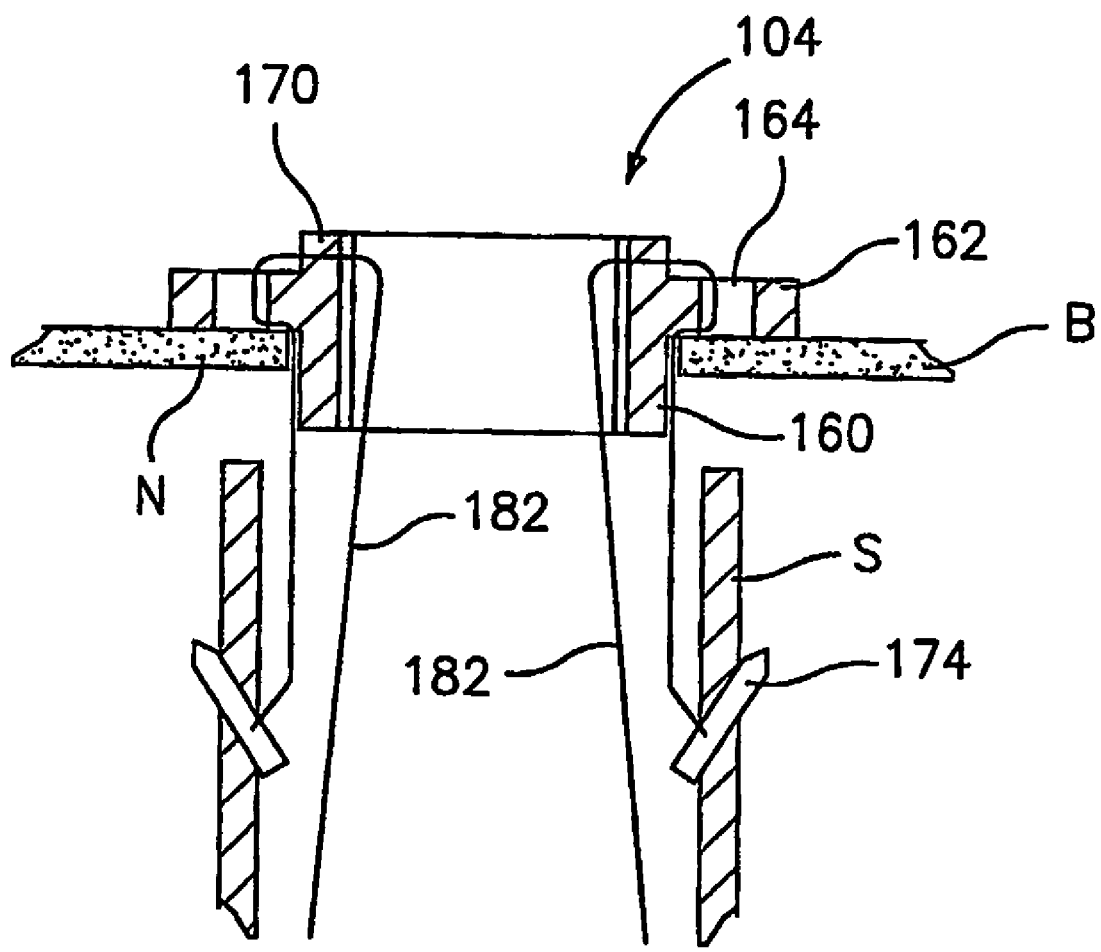
FIG. 20 is a cross-sectional elevational view of the device, as seen in FIG. 18, being withdrawn proximally through the urethral stump.

Instrument "I" is withdrawn proximally through urethra "U" until sutures 182 draw fitting 104 together with bladder "B" into contact with the distal end of urethral stump "S". As seen in FIGS. 18-20 and as described above, with fitting 104 in place, sutures 182 are secured to the inner wall of urethral stump "S" by anchors 174, run along the inner wall of urethral stump "S" and between annular sleeve 160 of fitting 104 and the rim of bladder neck "N", through hole 164 and suture locking means 166 desirably formed in flange 162 of fitting 104, through grooves 172 of annular rim 170 and out through annular sleeve 160. As instrument "I" and cartridge 102 are withdrawn, sutures 182 are drawn distally through suture locking means 166. Suture locking means 166 are configured and adapted to permit distal movement of sutures 182 therethrough and to prevent proximal movement of sutures 182 therethrough. In this manner, as sutures 182 are drawn distally through suture locking means 166, bladder neck "N" is drawn toward urethral stump "U" thereby tightening the anastomosis, however, if bladder neck "N" tries to separate from urethral stump "S", suture locking means 166 will prevent sutures 182 from withdrawing proximally through holes 164 and thereby loosening the anastomosis. For example, the suture locking means may comprise a construction for engaging the sutures or for engaging a feature on the sutures, such as knots.

As the anastomosis is tightened (i.e., bladder neck "N" is drawn toward urethral stump "S"), anchoring cones 168 formed on the proximal surface of flange 162 of fitting 104 become increasingly imbedded into the inner mucosal wall of bladder neck "N" thereby preventing the unwanted shifting of fitting 104 after the anastomosis has been tightened. Once the anastomosis has been tightened and sutures 182 securely held in suture locking means 166, the distal ends 184 of sutures 182 are cut to thereby release cartridge 102 from device 100. With device 100 properly in place and the anastomosis properly completed, the remainder of the prostatectomy is completed according to known methods and techniques.

In further embodiments, the fitting may comprise an expandable anchor for engaging a body vessel may, including those disclosed in certain embodiments of the following PCT Applications, all filed on an even date herewith: application entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Expandable Member, invented by Russell Heinrich and Scott Manzo; Method And Apparatus For Anastomosis Including An Anchoring Sleeve, invented by Scott Manzo; Method and Apparatus for Radical Prostatectomy Anastomosis, invented by Scott Manzo; the disclosures of which are all hereby incorporated by reference herein, in their entirety.

The deployable sutures may comprise any of the arrangements for deploying sutures disclosed in certain embodiments of the following PCT Applications, all filed on an even date herewith: Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo, the disclosures of which are all hereby incorporated by reference herein, in their entirety.

The methods and apparatus disclosed herein may be used for approximating and/or joining the urethra and bladder, intestinal portions of the body, blood vessels or any other body vessels.

While the above described device has been described as being used in connection with a radical prostatectomy, it is envisioned that devices having a similar structure and mode of operation can be used in various other surgical procedures. It will be understood that various modifications may be made to the embodiments of the presently disclosed anastomosis device and method disclosed herein. Therefore, the above description should not be construed as limiting, but merely as exemplifications of preferred embodiments. Those skilled in the art will envision other modifications within the scope and spirit of the present disclosure.

What is claimed is:

1. A device for joining a first body vessel with a second body vessel, comprising:
    an anchor fitting having a flange for engaging the first body vessel, said flange including a plurality of holes formed therethrough;
    a cartridge having an aperture and being removably coupled to a proximal end of said anchor fitting, said cartridge including:
        a body having a distal end and a plurality of longitudinal channels defined in the body, each longitudinal channel being open on said body at said distal end;
        a plurality of drive wires adapted to be received in a respective one of said longitudinal channels of said body;
    a plurality of needle anchors adapted to be seated within a respective one of said channels, each of the needle anchors having a pointed distal end; and
    a plurality of sutures, wherein each respective suture of said plurality of sutures is secured to one of said needle anchors, threaded through said holes formed in said flange of said anchor fitting and through said aperture of said cartridge.

2. The anastomosis device of claim 1, further comprising a suture lock provided in each of said holes, said suture lock being adapted to permit said sutures to be drawn distally through said holes and to prevent said sutures from being withdrawn proximally through said holes.

3. The anastomosis device of claim 1, wherein said flange includes a plurality of anchoring members formed along a proximal surface thereof for engaging a body vessel.

4. The anastomosis device of claim 1, further comprising a hub disposed on said body and arranged for engaging said drive wires, said drive wires being displaced distally by distal movement of said drive wires.

5. The anastomosis device of claim 1, wherein said anchor fitting is made of a bioabsorbable material.

6. The anastomosis device of claim 1, wherein each of said plurality of needle anchors is made of a bioabsorbable material.

7. The anastomosis device of claim 1, wherein each of said plurality of sutures is made of a bioabsorbable material.

8. An anastomosis device, comprising:
    a cartridge having an aperture and having a plurality of needle anchors slidably disposed in a plurality of channels formed in said cartridge and a pusher assembly adapted to push each of said plurality of needle anchors out of said channels of said cartridge;
    an anchor fitting removably coupled to a distal end of said cartridge, said anchor fitting including a flange having a plurality of holes, wherein each of said plurality of holes includes a suture lock adapted to permit a suture to be drawn distally through each of said plurality of holes and to prevent said sutures from being drawn proximally through each of said plurality of holes; and a plurality of sutures passing through a respective hole of said plurality of holes and secured to a respective needle anchor, and extending through said aperture of said cartridge.

9. The anastomosis device of claim 8, wherein said cartridge further comprises:
a body having an enlarged distal end and a plurality of longitudinal channels, wherein each longitudinal channel terminates in an angled channel.

10. The anastomosis device of claim 9, wherein said pusher assembly further comprises:
a hub adapted to be received on said body, said hub including a flange formed at a proximal end thereof; and
a plurality of drive wires received in a respective one of said longitudinal channels, each drive wire terminating in an angled distal tip corresponding to said angled channels, said drive wires being disposed adjacent said hub so that distal movement of said hub moves said drive wires distally.

11. The anastomosis device of claim 10, wherein said pusher assembly further comprises:
a compression spring disposed around said central shaft and between said flange of said hub and a distal end of said body.

12. The anastomosis device of claim 10, wherein each of said needle anchors is adapted to be seated on a respective angled distal tip of said plurality of drive wires, wherein a distal movement of said hub along said central shaft drives said plurality of angled distal tips against said needle anchors seated thereon and expels said needle anchors from said channels.

13. The anastomosis device of claim 12, wherein said cartridge includes a cover for enclosing said body and said pusher assembly therein, said cover includes a proximal head arranged for engagement by an instrument.

14. The anastomosis device of claim 8, wherein said anchor fitting is made of a bio-absorbable material.

15. The anastomosis device of claim 8, wherein each of said needle anchors is made from a bio-absorbable material.

16. The anastomosis device of claim 8, wherein each of said sutures is made from a bio-absorbable material.

17. The anastomosis device of claim 8, wherein said flange of said anchor fitting includes a plurality of anchoring members formed on a proximal surface thereof.

18. An anastomosis device, comprising:
a cartridge having a plurality of needle anchors retained therein and a pusher assembly slidably disposed within said cartridge, said pusher assembly being arranged to engage each needle anchor and to deploy said plurality of needle anchors out of said cartridge by moving said pusher assembly distally within said cartridge;
an anchor fitting for engaging a body vessel including an annular sleeve operatively coupled to a distal end of said cartridge and a flange formed on a distal end of said annular sleeve, said flange including a plurality of holes formed therein with each hole having a suture lock; and
a plurality of sutures, wherein a single suture is secured to a respective needle anchor and extends through a respective hole in said flange of said anchor fitting, and proximally through said annular sleeve of said anchor fitting, whereby when said cartridge is separated from said anchor fitting, said sutures are drawn proximally through said anchor fitting thereby drawing said needle anchors toward said anchor fitting.

19. The anastomosis device of claim 17, wherein said anchor fitting further comprises a body and an enlarged distal end; a plurality of longitudinal channels for receiving said needle anchors.

20. The anastomosis device of claim 19, wherein said longitudinal channels include distally angled channels formed in said enlarged distal end for receiving said needle anchors therein.

21. The anastomosis device of claim 20, wherein said pusher assembly further comprises a hub slidably received on said body and a plurality of drive wires wherein each of said drive wires is configured and adapted to be received in a respective one of said longitudinal channels of said body.

22. The anastomosis device of claim 21, wherein said anchor fitting further comprises a compression spring disposed about said central shaft and said drive wires and between said hub of said pusher assembly and a proximal surface of said body.

23. The anastomosis device of claim 22, wherein said cartridge further comprises a cover configured and adapted to enclose said central shaft and said pusher assembly therein, said cover including a proximal head.

24. The anastomosis device of claim 19, wherein said flange of said anchor fitting includes a plurality of anchoring members formed on a proximal surface thereof.

25. The anastomosis device of claim 19, wherein said suture lock is configured and adapted to permit said sutures to be drawn distally through said holes formed in said flange and to prevent said sutures from being withdrawn proximally through said holes.

26. A method of approximating a first body vessel with a second body vessel, comprising:
inserting an anchor fitting of an anastomosis device into the first body vessel;
passing an instrument into the second body vessel;
coupling the instrument to the anastomosis device;
disposing the anastomosis device within the second body vessel so that needle anchors of the anastomosis device are within the second body vessel;
deploying the needle anchors from the anastomosis device into the second body vessel; and
withdrawing sutures proximally, the sutures being attached to the needle anchors, and threaded through the anchor fitting, so that the needle anchors and the anchor fitting are moved toward one another.

27. The method according to claim 26, further comprising the steps of:
withdrawing the instrument thereby separating the anchor fitting from the device and tightening the anastomosis by drawing the sutures through an annular sleeve of the anchor fitting.

28. An anastomosis device, comprising:
an anchor fitting having a collar and a flange extending radially outward therefrom, the flange includes a plurality of openings formed therein, wherein each opening includes a suture lock configured and adapted to permit unidirectional passage of a suture therethrough;
a cartridge removably coupled to a proximal end of the fitting, the cartridge including:
a body having a plurality of substantially longitudinally oriented channels with a distal end of each channel terminating in a radially angled channel;
a pusher having a central bore and a hub slidably coupled thereto;
a plurality of drive wires operatively coupled to the hub, each drive wire being configured and adapted to be received in a respective longitudinal channel and having a distal end terminating in a tip configured and adapted to be received in a respective radially angled channel of the body; and a cover slidably disposed about the body and the pusher;

a plurality of needle anchors configured and adapted to be seated within a respective one of the radially angled channels of the body, each needle anchor being provided with means for coupling to a distal end of a respective drive wire; and a plurality of sutures, wherein suture is secured to an outer surface of a respective needle anchor, threaded through the openings holes formed in the flange of the anchor fitting, through the collar of the anchor fitting and anchored to an inner surface of the cartridge.

* * * * *